(12) United States Patent
Zappacosta et al.

(10) Patent No.: US 8,876,866 B2
(45) Date of Patent: Nov. 4, 2014

(54) SPINOUS PROCESS FUSION DEVICES AND METHODS THEREOF

(75) Inventors: Jason Zappacosta, Philadelphia, PA (US); Daniel Laskowitz, Lancaster, PA (US); William E. Duffield, Collegville, PA (US); Jason Cianfrani, East Norriton, PA (US); Jody L. Seifert, Birdsboro, PA (US); Darren Clutter, Palm, PA (US)

(73) Assignee: Globus Medical, Inc., Audubon, PA (US)

( * ) Notice: Subject to any disclaimer, the term of this patent is extended or adjusted under 35 U.S.C. 154(b) by 129 days.

(21) Appl. No.: 12/966,662

(22) Filed: Dec. 13, 2010

(65) Prior Publication Data

US 2012/0150228 A1 Jun. 14, 2012

(51) Int. Cl.
*A61B 17/70* (2006.01)
*A61B 17/02* (2006.01)

(52) U.S. Cl.
CPC ..... *A61B 17/7068* (2013.01); *A61B 2017/0256* (2013.01)
USPC .......................................................... 606/248

(58) Field of Classification Search
CPC ........... A61B 17/7062; A61B 17/7065; A61B 17/7067; A61B 17/7068
USPC ................................................. 606/247–249
See application file for complete search history.

(56) References Cited

U.S. PATENT DOCUMENTS

| | | | |
|---|---|---|---|
| 3,056,852 A * | 10/1962 | Sachs | 174/153 G |
| 4,116,104 A * | 9/1978 | Kennedy | 411/427 |
| 4,349,921 A | 9/1982 | Kuntz | |
| 4,863,476 A | 9/1989 | Shepperd | |
| 4,863,477 A | 9/1989 | Monson | |
| 5,390,683 A | 2/1995 | Pisharodi | |
| 5,645,596 A | 7/1997 | Kim et al. | |
| 5,665,122 A | 9/1997 | Kambin | |
| 6,039,761 A | 3/2000 | Li | |
| 6,045,579 A | 4/2000 | Hochshuler et al. | |
| 6,080,193 A | 6/2000 | Hochshuler et al. | |
| 6,099,531 A | 8/2000 | Bonutti | |
| 6,126,689 A | 10/2000 | Brett | |
| 6,176,882 B1 | 1/2001 | Biedermann et al. | |
| 6,258,125 B1 | 7/2001 | Paul et al. | |
| 6,287,308 B1 * | 9/2001 | Betz et al. | 606/263 |
| 6,364,883 B1 * | 4/2002 | Santilli | 606/279 |
| 6,554,863 B2 | 4/2003 | Paul et al. | |
| 6,562,074 B2 | 5/2003 | Gerbec | |
| 6,576,016 B1 | 6/2003 | Hochshuler et al. | |
| 6,641,614 B1 | 11/2003 | Wagner et al. | |
| 6,648,917 B2 | 11/2003 | Gerbec | |
| 6,666,891 B2 | 12/2003 | Boehm, Jr. | |
| 6,692,495 B1 | 2/2004 | Zacouto | |

(Continued)

FOREIGN PATENT DOCUMENTS

| | | |
|---|---|---|
| WO | 2006045094 A2 | 4/2006 |
| WO | 2006113080 A2 | 10/2006 |
| WO | 2008044057 A1 | 4/2008 |

*Primary Examiner* — Mary Hoffman (57) ABSTRACT

The present application discloses a device for positioning and immobilizing at least two adjacent vertebrae. In particular, in one or more embodiments, the spinous process fusion devices can distract and immobilize the spinous processes of adjacent vertebrae. The spinous process fusion devices can include a rod, a first wing, and a second wing. The rod may include one or more ratchet receivers in the form of proturbances that interact with ratchets on the second wing.

14 Claims, 11 Drawing Sheets

(56) References Cited

U.S. PATENT DOCUMENTS

| | | |
|---|---|---|
| 6,706,070 B1 | 3/2004 | Wagner et al. |
| 6,752,832 B2 | 6/2004 | Neumann |
| 6,830,589 B2 | 12/2004 | Erickson |
| 6,849,093 B2 | 2/2005 | Michelson |
| 6,852,129 B2 | 2/2005 | Gerbec |
| 6,863,673 B2 | 3/2005 | Gerbec |
| 6,881,228 B2 | 4/2005 | Zdeblick |
| 7,018,415 B1 | 3/2006 | Mckay |
| 7,217,291 B2 | 5/2007 | Zucherman |
| 7,282,063 B2 | 10/2007 | Cohen et al. |
| 7,547,325 B2 | 6/2009 | Biedermann et al. |
| 7,621,953 B2 | 11/2009 | Braddock, Jr. |
| 7,641,693 B2 | 1/2010 | Gütlin |
| 7,682,396 B2 | 3/2010 | Beaurain |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent |
| 7,837,734 B2 | 11/2010 | Zucherman |
| 7,875,078 B2 | 1/2011 | Wysocki |
| 2002/0045945 A1 | 4/2002 | Liu |
| 2003/0040746 A1* | 2/2003 | Mitchell et al. ............ 606/61 |
| 2003/0216736 A1* | 11/2003 | Robinson et al. ............ 606/61 |
| 2004/0049271 A1 | 3/2004 | Biedermann et al. |
| 2004/0153065 A1 | 8/2004 | Lim |
| 2005/0033432 A1 | 2/2005 | Gordon |
| 2005/0149188 A1 | 7/2005 | Cook et al. |
| 2005/0171541 A1 | 8/2005 | Boehm, Jr. |
| 2005/0273171 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0058878 A1 | 3/2006 | Michelson |
| 2006/0122701 A1 | 6/2006 | Kiester |
| 2006/0129244 A1 | 6/2006 | Ensign |
| 2006/0149385 A1 | 7/2006 | Mckay |
| 2006/0195192 A1 | 8/2006 | Gordon |
| 2006/0229729 A1 | 10/2006 | Gordon |
| 2006/0247640 A1* | 11/2006 | Blackwell et al. ............ 606/71 |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings |
| 2007/0055377 A1 | 3/2007 | Hanson |
| 2007/0185490 A1* | 8/2007 | Implicito ............ 606/61 |
| 2007/0191951 A1 | 8/2007 | Branch, Jr. |
| 2008/0021559 A1 | 1/2008 | Thramann |
| 2008/0065222 A1 | 3/2008 | Hamada |
| 2008/0140207 A1 | 6/2008 | Olmos |
| 2008/0147190 A1* | 6/2008 | Dewey et al. ............ 623/17.16 |
| 2008/0167657 A1 | 7/2008 | Greenhalgh |
| 2008/0177319 A1* | 7/2008 | Schwab ............ 606/257 |
| 2008/0183204 A1 | 7/2008 | Greenhalgh |
| 2008/0183211 A1* | 7/2008 | Lamborne et al. ............ 606/249 |
| 2008/0243189 A1* | 10/2008 | Purcell et al. ............ 606/264 |
| 2008/0281346 A1 | 11/2008 | Greenhalgh |
| 2008/0288073 A1 | 11/2008 | Renganath |
| 2008/0300598 A1 | 12/2008 | Barreiro et al. |
| 2008/0312741 A1* | 12/2008 | Lee et al. ............ 623/17.11 |
| 2008/0319549 A1 | 12/2008 | Greenhalgh |
| 2009/0005784 A1* | 1/2009 | Blain et al. ............ 606/90 |
| 2009/0024217 A1 | 1/2009 | Levy et al. |
| 2009/0125062 A1 | 5/2009 | Arnin |
| 2009/0149956 A1 | 6/2009 | Greenhalgh |
| 2009/0149959 A1 | 6/2009 | Conner |
| 2009/0198338 A1* | 8/2009 | Phan ............ 623/17.16 |
| 2009/0204218 A1 | 8/2009 | Richelsoph |
| 2009/0222100 A1 | 9/2009 | Cipoletti |
| 2009/0240334 A1 | 9/2009 | Richelsoph |
| 2009/0270989 A1 | 10/2009 | Conner |
| 2009/0281628 A1 | 11/2009 | Oglaza |
| 2009/0292316 A1* | 11/2009 | Hess ............ 606/249 |
| 2009/0292361 A1 | 11/2009 | Lopez |
| 2009/0299478 A1 | 12/2009 | Carls |
| 2010/0036419 A1* | 2/2010 | Patel et al. ............ 606/249 |
| 2010/0049324 A1 | 2/2010 | Valdevit |
| 2010/0070041 A1 | 3/2010 | Peterman |
| 2010/0082109 A1 | 4/2010 | Greenhalgh |
| 2010/0087860 A1* | 4/2010 | Chin et al. ............ 606/249 |
| 2010/0179657 A1 | 7/2010 | Greenhalgh |
| 2010/0185291 A1 | 7/2010 | Jimenez |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222817 A1* | 9/2010 | Perez-Cruet et al. ............ 606/249 |
| 2010/0222884 A1 | 9/2010 | Greenhalgh |
| 2010/0234889 A1* | 9/2010 | Hess ............ 606/249 |
| 2010/0234952 A1 | 9/2010 | Peterman |
| 2010/0249933 A1 | 9/2010 | Trieu |
| 2010/0280622 A1 | 11/2010 | Mckinley |
| 2010/0286779 A1 | 11/2010 | Thibodeau |
| 2010/0286780 A1 | 11/2010 | Dryer |
| 2010/0292796 A1 | 11/2010 | Greenhalgh |
| 2010/0305705 A1 | 12/2010 | Butler |
| 2010/0318127 A1* | 12/2010 | Phan et al. ............ 606/249 |
| 2010/0331981 A1 | 12/2010 | Mohammed |
| 2010/0331985 A1 | 12/2010 | Gordon |
| 2011/0022090 A1* | 1/2011 | Gordon et al. ............ 606/249 |
| 2011/0035011 A1 | 2/2011 | Cain |
| 2011/0066186 A1* | 3/2011 | Boyer et al. ............ 606/249 |
| 2011/0093074 A1 | 4/2011 | Glerum |
| 2011/0144692 A1* | 6/2011 | Saladin et al. ............ 606/249 |
| 2011/0319939 A1* | 12/2011 | Kretzer et al. ............ 606/264 |

* cited by examiner

SPINOUS PROCESS FUSION DEVICES AND METHODS THEREOF

FIELD OF THE INVENTION

The present disclosure generally relates to a device for positioning and immobilizing at least two adjacent vertebrae. In particular, in one or more embodiments, the present disclosure relates to spinous process fusion devices that distract and/or immobilize the spinous processes of adjacent vertebrae.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

Typically, weaknesses in the spine are corrected by using devices that fuse one or more vertebrae together. Common devices involve plate systems that align and maintain adjacent vertebrae in a desired position, with desired spacing. These devices, commonly referred to as bone fixation plating systems, typically include one or more plates and screws for aligning and holding vertebrae in a fixed position with respect to one another. When implanting these devices in a patient, it may be desirable for interspinous distraction, for example, to obtain a desired spacing between the fused spinous processes.

Thus, there is a need for a device that provides structural stability to adjacent vertebrae, for example, a plate system that can distract and/or immobilize the spinous processes of adjacent vertebrae.

SUMMARY

An embodiment of the present invention provides an implantable device. The implantable device may comprise a rod, a first wing coupled to the rod, and a second wing, wherein a ratcheting lock secures the second wing to the rod.

The features and advantages of the present invention will be readily apparent to those skilled in the art. While numerous changes may be made by those skilled in the art, such changes are within the spirit of the invention.

DETAILED DESCRIPTION OF THE ILLUSTRATED EMBODIMENTS

The present disclosure generally relates to a device for positioning and immobilizing at least two adjacent vertebrae. In particular, in one or more embodiments, the present disclosure relates to spinous process fusion devices that distract and/or immobilize the spinous processes of adjacent vertebrae. The fusion devices may be implanted in a patient, for example, without the need for removal of the supraspinous ligament. In certain embodiments, the fusion devices provide for distraction of the interspinous space, for example, allowing use of the device as a spacer and a clamp.

Figure 1:
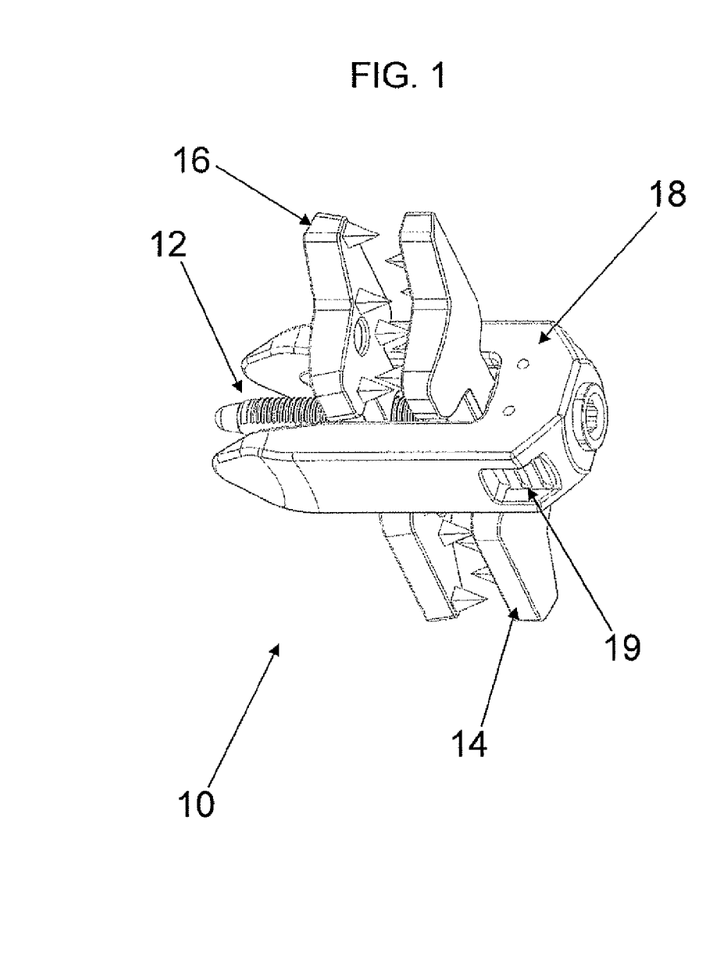
FIG. 1 is a perspective view of one embodiment of a spinous process fusion device of the present invention having a ratcheting lock.
Figure 2:
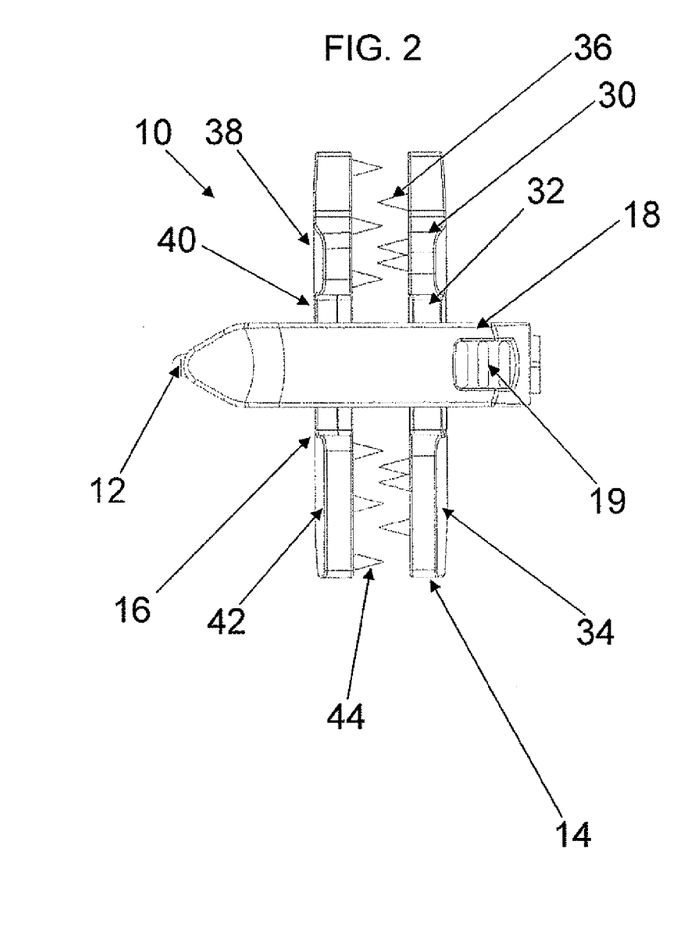
FIG. 2 is a lateral view of the spinous process fusion device of FIG. 1.
Figure 3:
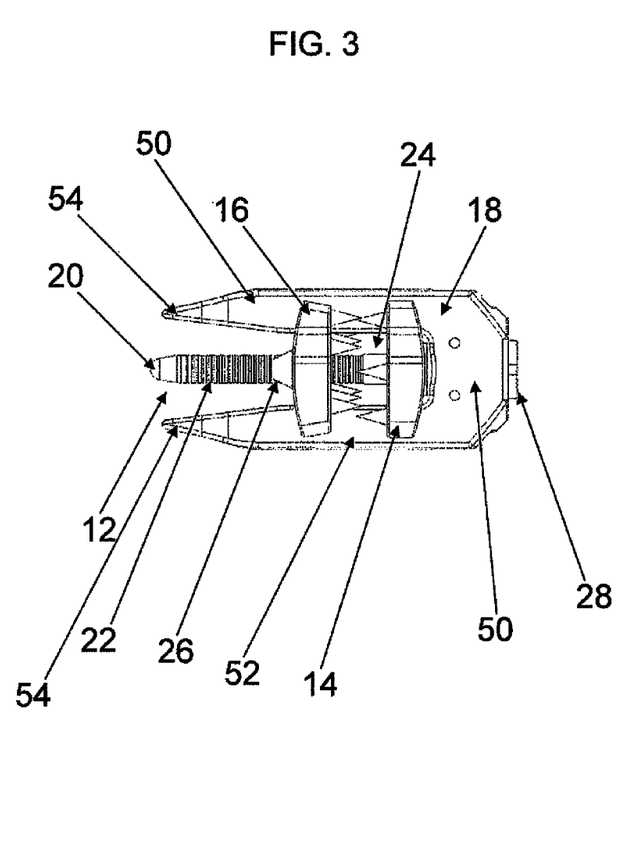
FIG. 3 is a top view of one embodiment of the spinous process fusion device of FIG. 1.

FIGS. 1-3 illustrate a spinous process fusion device 10 in accordance with one embodiment of the present invention. As illustrated, the spinous process fusion device 10 may comprise a rod 12, a first wing 14, a second wing 16 and a central barrel 18. In accordance with embodiments of the present invention, the first wing 14 and the second wing 16 may be secured by the rod 12 which is coupled to the central barrel 18. When installed in a patient, the first wing 14 and the second wing 16 may engage spinous processes of adjacent vertebra above and below the interspinous space. The device 10 should thus, for example, immobilize the lumbar motion segment associated with the vertebrae of the engaged spinous processes. In certain embodiments, the device 10 should immobilize the lumbar motion segment without the need for additional devices.

In the preferred embodiment, the rod 12 may have a length, for example, of about 20 millimeters to about 50 millimeters. As illustrated, the rod 12 extends from a first end to a second end. The first end of the rod 12 is coupled to the central barrel 18 through an opening in the central barrel 18. The second end of the rod 12 is tapered to be configured as a frustoconical tip 20. The rod 12 further may include ratchet receivers 22 on opposing sides of the rod 12 that comprise protuberances. The protuberances may be, for example, in the shape of an inclined wedge with the inclined portion of the protuberance extending in the direction of the tapered end of the rod 12. The protuberances of the ratchet receivers may be arranged along the longitudinal axis of the rod 12. The protuberances 12 further may be arranged in various positions on a first and a second side of the rod 12. In the illustrated embodiment, the protuberances of the ratchet receivers 22 are integrally formed with the rod 12.

The rod 12 is also provided with a portion 24 proximal to the first end that does not have ratcheting teeth or threads that is coupled to the first wing 14. The first wing 14 is configured to be angulated with the portion 24 proximal to the first end of the rod 12. The second wing 16 is configured with a hole which can receive the second end of the rod 12. The second wing 16 is also provided with extensions or ratchets 26 positioned on either side of the second wing 16. Each one of the extensions or ratchets 26 are adapted to couple with the protuberances of the ratchet members 22. As force is applied upon the second wing 16, the second wing 16 is moved toward the first wing 14 along the rod 12.

An embodiment of the first wing 14 will be described in more detail with respect to FIGS. 1-5. The first wing 14 may extend transversely from the rod 12 and the barrel 18 and be disposed over the portion proximal 24 to the first end of the rod 12 and the head 28. The first wing 14 may have a length sufficient to span, for example between adjacent spinous processes, such as about 20 millimeters to about 60 millimeters. The first wing 14 may comprise an upper portion 30, a central portion 32, a lower portion 34, and teeth 36. The upper portion 30 and the lower portion 34 may have widths respectively of about 10 millimeters to about 80 millimeters, while the central portion 32 may have a width of about 5 millimeters to about 10 millimeters. In the illustrated embodiment, the upper portion 30 and the lower portion 34 are each generally rectangular in shape. It should be understood that other shapes for these portions of the first wing 14 may also be suitable. By way of example, the wing 14 may be rectangular with rounded corners, oval, circular, football shaped, wedge-shaped, and a variety of other shapes suitable for a particular application.

In alternative embodiment of the first wing 14, each of the upper portion 30 and the lower portion 34 may have a cutout, for example, to facilitate stacking of more than one spinous process fusion device 10. The cutout may be configured so that the upper portion 30 and the lower portion 34 of the first wing 14 mate. In this manner, an upper portion 14 of one spinous process fusion device 10 may engage the same spinous process as the lower portion of another fusion device 10. While not illustrated, the first wing 14 may be configured to angulate on the connector portion or portion 24 proximal to the first end of the rod 12, for example, to conform to the patient's anatomy. By way of example, the first wing 14 may be configured to rotate about its longitudinal axis.

Referring again to FIGS. 1-5, the central portion 32 of the first wing 14 may have an opening that should allow the first wing 14 to be placed onto the connector portion 24. The opening should be configured so that the first wing 14 cannot be removed from the connecting portion 24 over the rod 12. The first wing 14 may include the teeth 36 (e.g., spikes) for engaging the spinous processes. By way of example, the teeth 36 may bite into the spinous processes clamping the spinous processes in position. As illustrated, the teeth 36 extend from the side of the first wing 14 that is facing the second wing 16.

Second wing 16 may be placed onto the rod 12 over the protuberances of the ratcheting receivers 22, in accordance with embodiments of the present invention. Second wing 16 may extend transversely from the rod 12. The second wing 16 may have a length sufficient to span, for example between adjacent spinous processes, such as about 20 millimeters to about 60 millimeters. As illustrated, the second wing 16 may comprise upper portion 38, central portion 40 and lower portion 42. The upper portion 38 and lower portion 42 may have widths respectively of about 10 millimeters to about 20 millimeters, while the central portion 40 may have a width of about 5 millimeters to about 10 millimeters. As described above with respect to the first wing 14, the upper portion 38 and the lower portion 42 of the second wing 16 may also be rectangular shaped or any other shape suitable for a particular application. In addition, to facilitate stacking, the upper portion 38 and the lower portion 42 may also have cutouts, in certain embodiments. The second wing 16 further may include teeth 44 (e.g., spikes) for engaging the spinous processes. The teeth 44 may, for example, bite into the spinous process clamping them in position. In the illustrated embodiment, the teeth 44 may extend from the side of the second wing 16 that is facing the first wing 14.

Referring now to FIGS. 6-12, the second wing 16 further may include an opening that should allow the second wing 16 to be placed onto the rod 12. The exterior wall of the second wing 16 surrounding the opening may include ratcheting members 46 that extend outwardly from the exterior wall of the second wing 16. The ratcheting members 46 are configured to extend from the exterior wall at one edge of the opening of the second wing 16. The ratcheting members 46 may be grooved so that it fits over a corresponding one of the protuberances of the ratcheting receivers 22. The ratcheting members 36 may be in the shape of an inclined wedge with the inclined portion in the opposite direction of the inclined portion of the protuberances so that the ratcheting members 46 fit into a space between adjacent protuberances. In alternative embodiments, additional ratcheting members may be utilized.

When the second wing 16 is placed over the rod 12, the ratcheting members 46 should interact with the ratcheting receivers 22 to create a one-way ratcheting lock, in accordance with embodiments of the present invention. By way of example, the ratcheting members 46 and the protuberances of the ratcheting receivers 22 should be configured so that, as the second wing 16 is slid onto the rod 14, the second wing 16 is movable over the protuberances. Once the second wing 16 is slid onto the rod 12, the ratcheting members 46 should engage the protuberances and prevent movement when the second wing 16 is urged in the opposite direction, for example, when removal of the second wing 16 from the rod 12 is attempted. The second wing 16, thus, may be ratcheted onto the rod 12. While the one-way ratcheting lock is described with respect to the illustrated embodiment, it should be understood that other techniques may be used for the one-way ratcheting lock in accordance with embodiments of the present invention.

Figure 8:
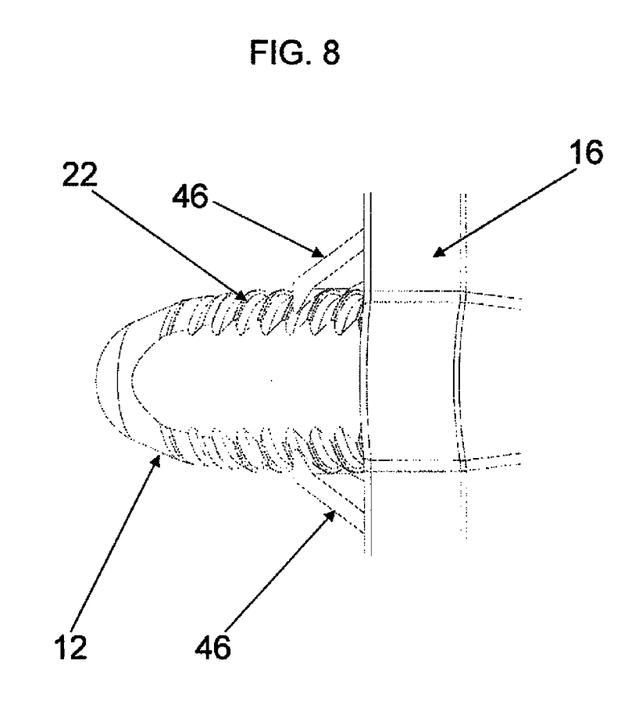
FIGS. 8-12 illustrate the cam locking and ratcheting mechanism associated with the spinous process fusion device according to the present invention.
Figure 9:
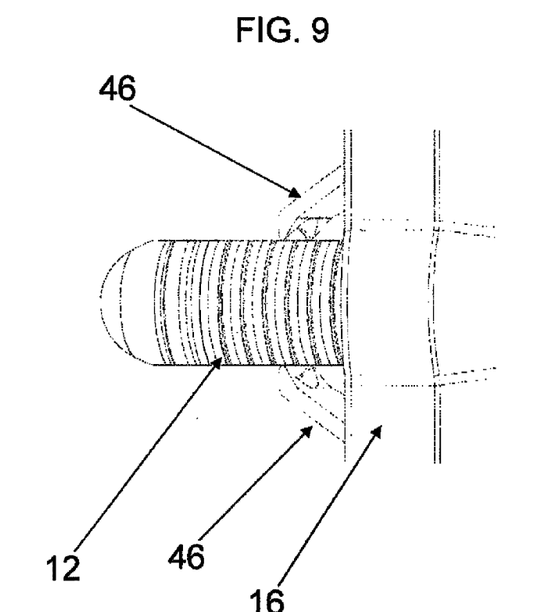
Figure 10:
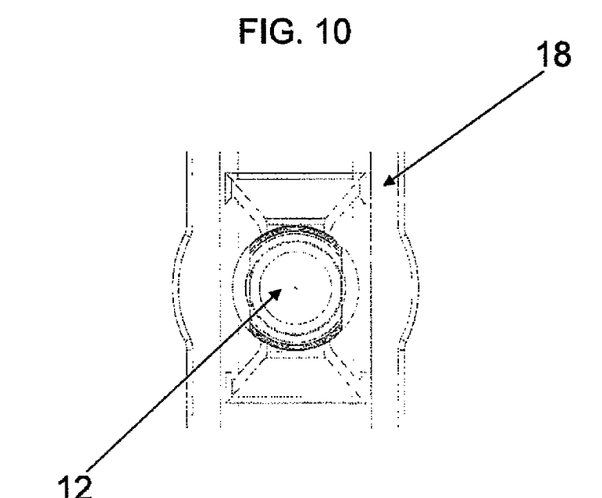
Figure 11:
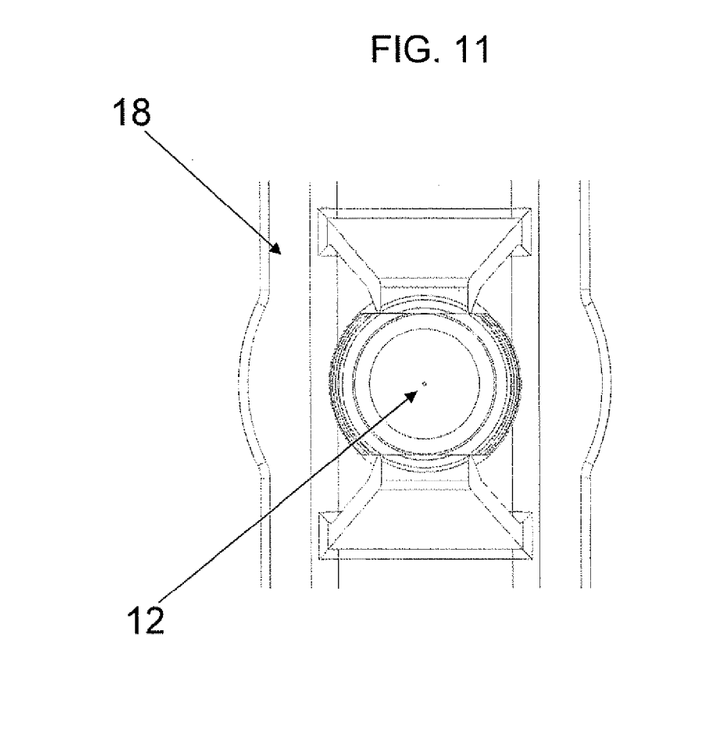
Figure 12:
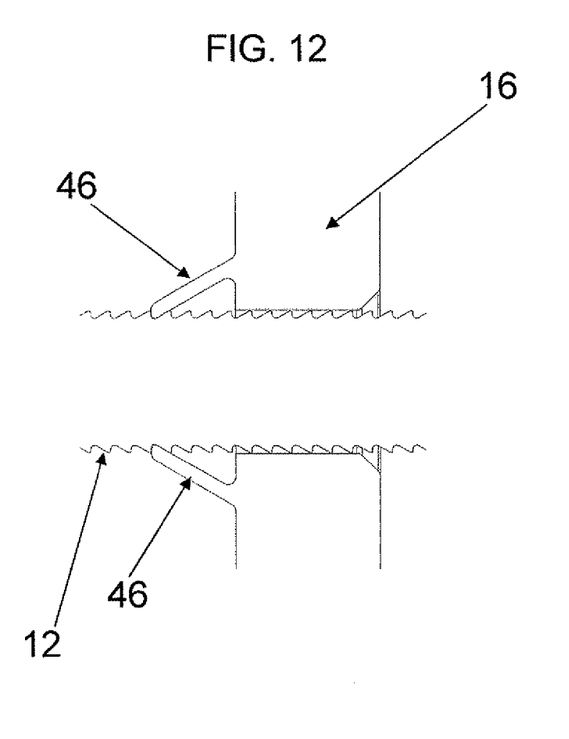

FIGS. 8-12 illustrate the ratcheting and locking mechanism of the present invention. Specifically, FIGS. 8 and 10 illustrate the rod 12 in a locked position. When the rod 12 is in a locked position, the protuberance of the ratchet receivers 22 are engaged with the ratchet extensions 46 of the second wing 16, the spinous process fusion device 10 is in a locked position, as illustrated in FIG. 12. FIGS. 9 and 11 illustrate the rod 12 in an unlocked position, wherein the ratchet extensions 46 do not engage with the protuberances of the ratchet receivers 22. To actuate the rod 12 from a locked to an unlocked position, an removal instrument is configured to adapt to couple with the head of the rod 12. When pressure is applied to the removal instrument, the rod 12 is moved from either a locked/unlocked position to the unlocked/locked position by disengaging the ratchet extensions 46 to the ratchet receivers 22 or engaging the ratchet receivers 22. In the preferred embodiment, the removal instrument can be actuated to turn the rod 90 degrees to position the rod in a locked position and turned 90 degrees further to position the rod 12 in an unlocked position.

Figure 4:
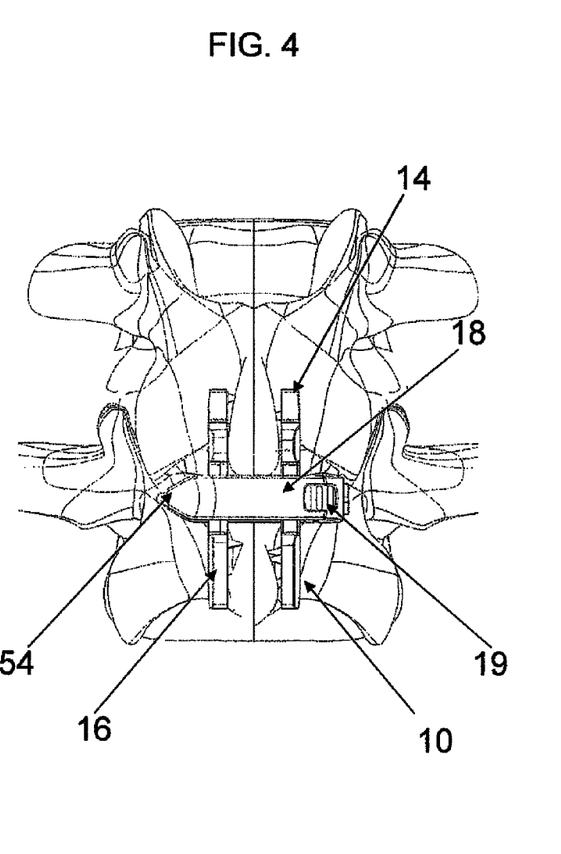
FIGS. 4 and 5 are views of the spinous process fusion device positioned between adjacent vertebrae.

Referring now to FIGS. 3 and 4, the central barrel 18 is discussed in greater detail. illustrated, spinous process fusion device 10 comprises the rod 12, the first wing 14, and the second wing 16. In the illustrated embodiment, the central barrel 18 comprises a first side 50 and second side 52, which each extend on either side of the rod 12. The first side 50 and the second side 52 may have widths respectively of about 10 millimeters to about 30 millimeters. Each of the first side 50 and the second side 52 may include a tapered end 54. The tapered end 54 should facilitate insertion of the spinous process fusion device 10 into the interspinous space between adjacent vertebrae. Moreover, the width of the first side 50 and the second side 52 generally should provide for distraction of the interspinous space during placement of the device 10. Thus, the device 10 may function, for example, as both a spacer and a clamp. Moreover, the first side 50 and the second side 52 generally should restrict and/or prevent rotation of the first wing 14 and the second wing 16 about the connecting portion 24 and the rod 12, respectively. As illustrated in FIG. 4, the central portion 32 of the first wing 14 may have a narrower width than the upper portion 30 and lower portion 34 thereof so that the upper portion 30 and the lower portion 34 may extend over the first side 50 and the second side 52 of the central barrel 18. Likewise, the central portion 40 of the second wing 16 may also have a narrower width than the upper portion 38 and the lower portion 42 thereof. As such, the central barrel 18 may act as a guide for the second wing 16 when it is inserted onto the rod 12 so that it is in alignment with the first wing 14. The central barrel 18 further may comprise an end 56 that connects the first side 50 and the second side 52. The central barrel 18 also comprises at least one insertion instrument connecting portions 19. In the preferred embodiment, connecting portions 19 are configured on opposing sides of the first and second sides 50, 52 of the central barrel 18. The connecting portions 19 are configured and adapted to couple with an insertion instrument. The connecting portions 19 can be configured in various embodiments for connecting to an insertion instrument, for instance, a dovetail connection for attaching to an insertion instrument can be utilized.

Figure 5:
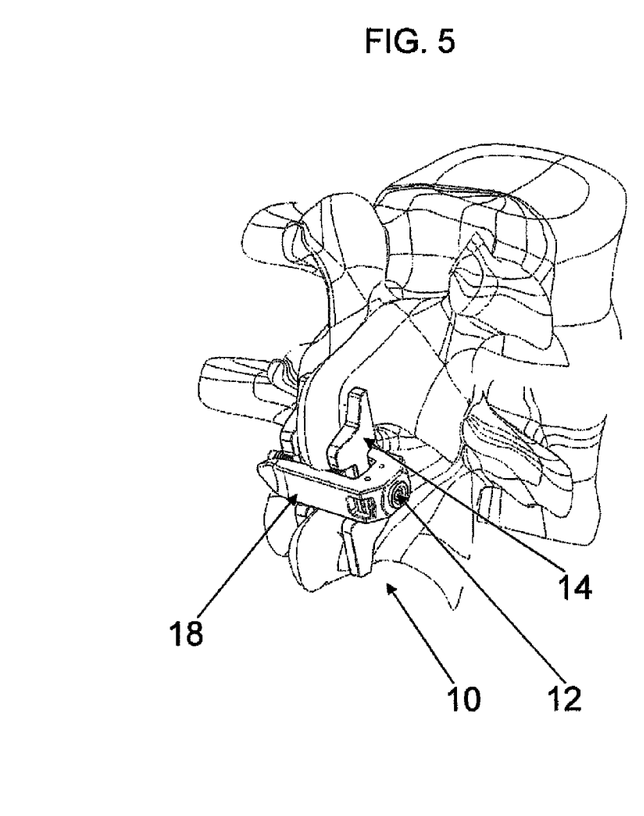

FIGS. 4 and 5 illustrate the spinous process fusion device 10 of FIGS. 1-3 positioned in the interspinous space between adjacent vertebrae. As illustrated in FIGS. 4 and 5, the first and second wing 14, 16 are firmly positioned in between the adjacent spinous process with the central barrel of the device 10 distracting the spinous processes. Bone graft may be implanted within the spinout process fusion device 10 and within the interspinous space to enable greater fusion in the interspinous space.

Figure 6:
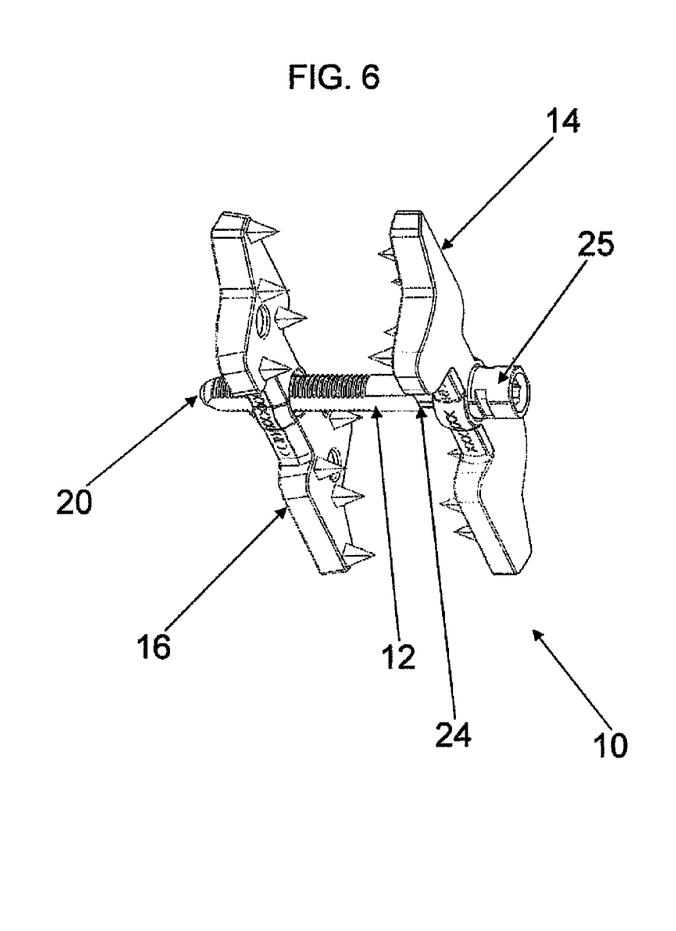
FIG. 6 is a perspective view of another embodiment of a spinous process fusion device according to the present invention.
Figure 7:
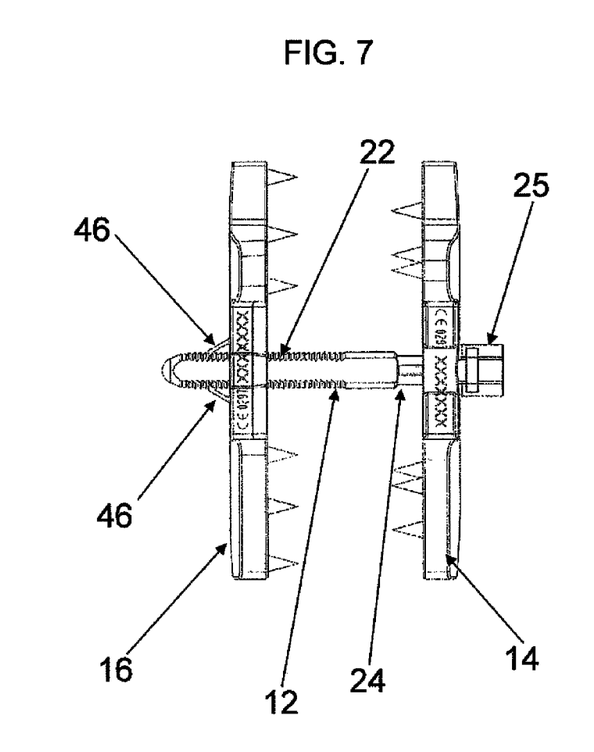
FIG. 7 is a top view of the spinous process fusion device of FIG. 6.

FIGS. 6 and 7 illustrate an another embodiment of the present invention. In this particular embodiment, a central barrel is not provided. In this embodiment, the implant 30 is comprised of a rod 12, a pivoting plate 14, and a locking plate 16. The rod 12 is coupled to the pivoting plate 14 through an opening in the pivoting plate 14. The rod 12 is configured with a first end and a second end. The first end of the rod 12 is tapered to be configured to be a frustoconical tip 20. The second end 24 is configured with a connection portion 24 and head 25 having a diameter greater than the diameter than the opening in the pivoting plate 14. The head 25 of the rod is configured to receive an instrument capable of actuating the rod at least 90 degrees in either direction. As in the embodiment illustrated in FIGS. 1-3, the rod 12 is also configured with ratchet receivers 22 on opposing sides of the rod 12. The ratchet receivers 22 comprise protuberances that extend from near the frustoconical tip 20 of the first end of the rod 12 to pivoting plate 14. The number of protuberances may be varied depending on a patient's anatomy.

As in the previous embodiment, the rod 12 is also provided with a portion proximal to the first end that does not have ratcheting teeth or threads that is coupled to the pivoting plate 14. The pivoting plate 14 is configured to be angulated with the portion proximal to the first end of the rod 12. The locking plate 16 is configured with a hole which can receive the second end of the rod 12. The locking plate 16 is also provided with extensions 46 positioned on either side of the locking plate 16. Each one of the extensions 16 is adapted to couple with the ratcheting members 22. As force is applied upon the locking plate 16, the locking plate 16 is moved toward the pivoting plate 14 along the rod 12.

Now turning to FIGS. 13-20, the method and implantation of the spinous fusion device will be described in greater detail. As explained above, the spinous process fusion device 10 may be implanted in a patient to, for example, immobilize the spinous processes of adjacent vertebrae. An embodiment of implanting the spinous process fusion device 10 in a patient may comprise inserting a spinous fusion device 10 comprising a rod and a first wing between adjacent spinous processes of a patient. The spinous fusion device 10 generally may be inserted until the teeth of the first wing engage the adjacent spinous processes both above and below the interspinous space. In certain embodiments, a second wing generally may not be on the device 10 when it is inserted. If used, the central barrel may provide for distraction of the interspinous space during placement of the device 10. However, it should be understood that additional techniques and/or devices may be used for distraction of the interspinous space. In addition, the design of the spinous process fusion device 10 generally should allow its insertion between adjacent spinous processes without removal of the supraspinous ligament. Once the spinous fusion process device 10 has been placed between the adjacent spinous processes, the second wing may be placed onto the rod such that the teeth of the second wing engage the adjacent spinous processes both above and below the interspinous space. The second wing generally may be positioned on the rod such that the first wing and the second wing clamp the spinous processes in place. The one-way ratcheting lock from interaction of the protuberances of the rod and the ratcheting members of the second wing generally should prevent removal of the second wing. In this manner, the lumbar motion segment may be immobilized, for example, without the need for additional devices.

Figure 13:
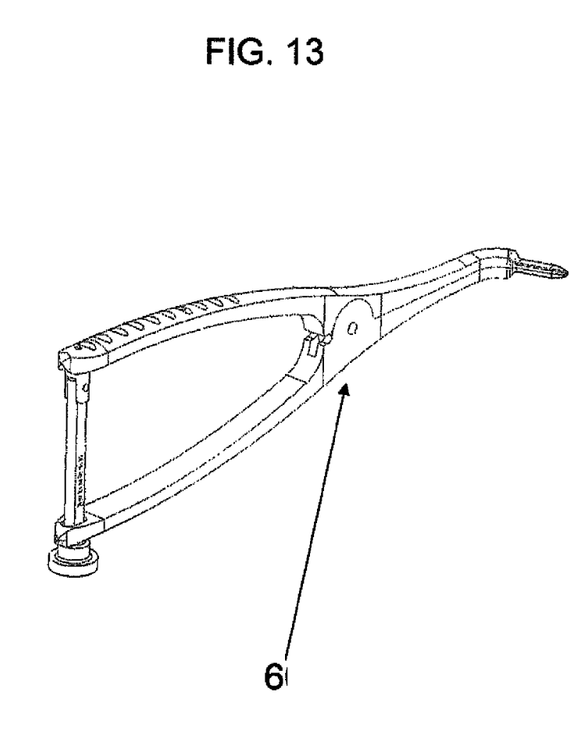
FIG. 13 is a perspective view of a distraction tool according to the present invention.
Figure 14:
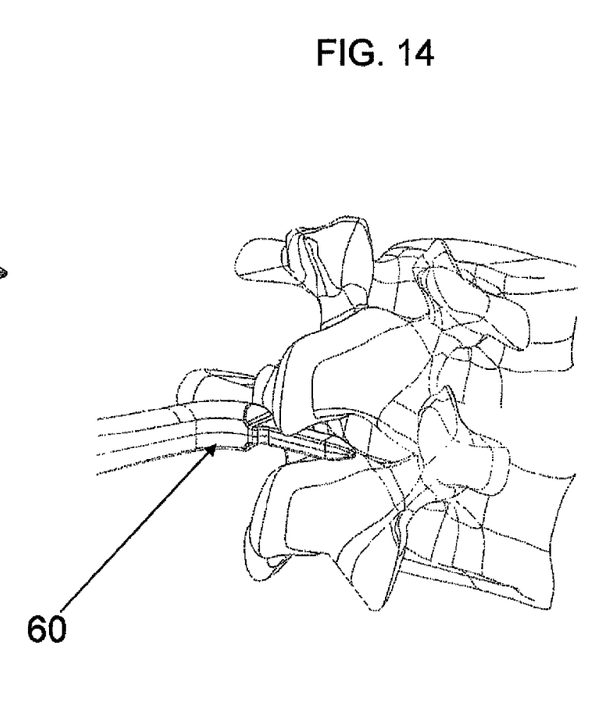
FIG. 14 is an illustration of the distraction tool positioned between adjacent spinous processes.
Figure 15:
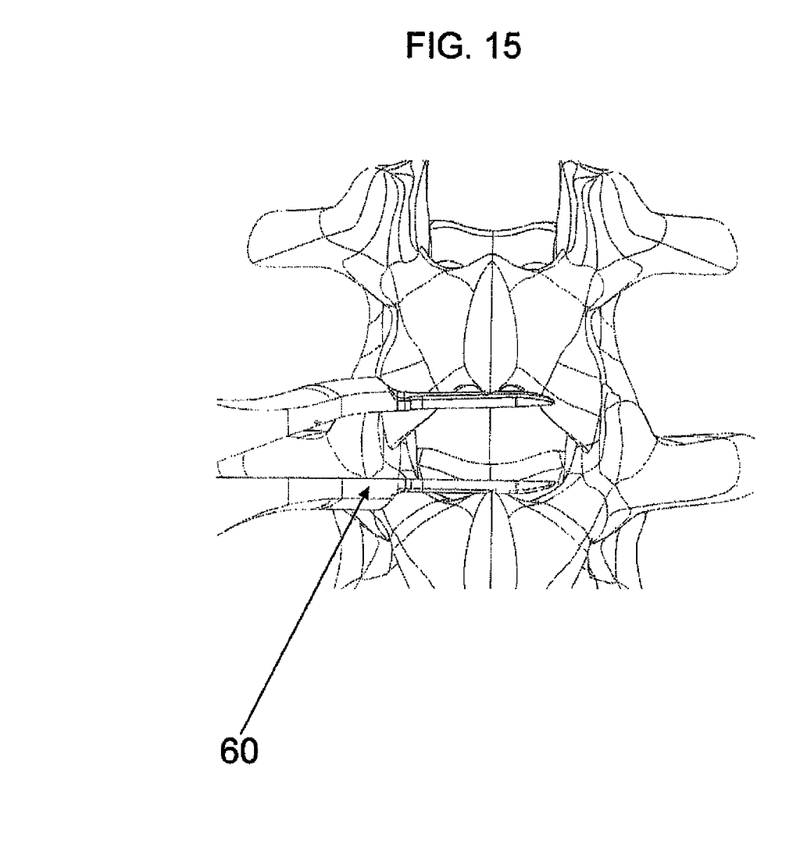
FIG. 15 illustrates the distraction of the adjacent spinous processes with a distraction tool according to the present invention.
Figure 16:
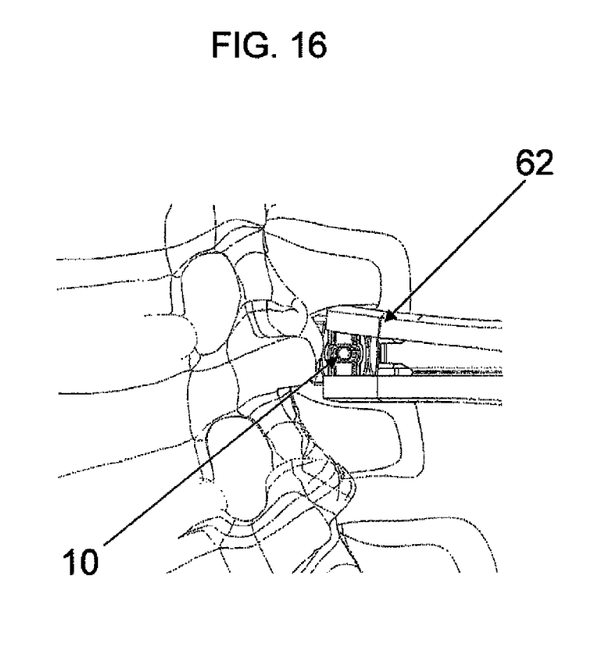
FIG. 16 illustrates the implantation of a spinous process fusion device between adjacent spinous processes.
Figure 17:
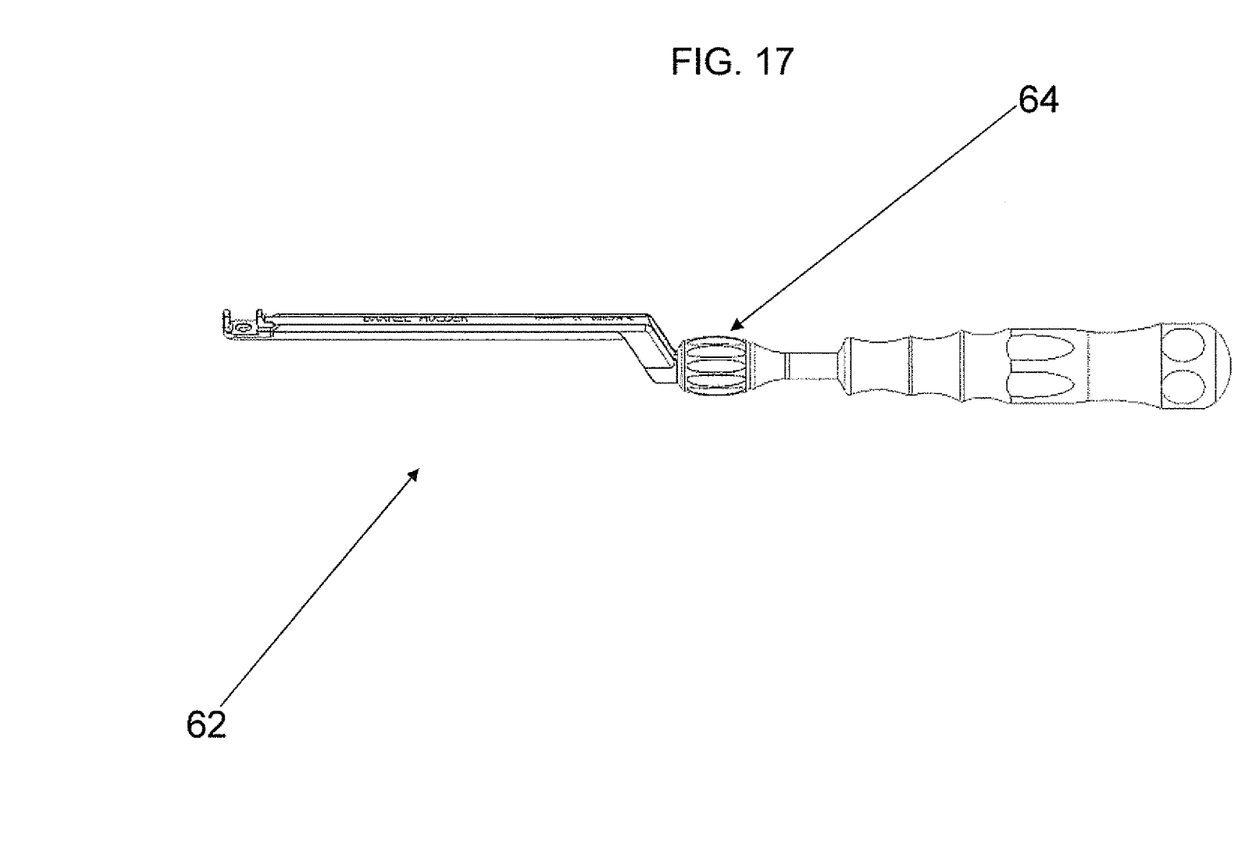
FIG. 17 illustrates an spinous process fusion device insertion instrument.

Specifically, FIGS. 13-15 illustrates a distraction tool 60 and the distraction of the interspinous space between adjacent spinous processes. During the surgical implantation of the spinous process fusion implant, the spinous processes are distracted to create space for the positioning of the implant according to one embodiment of the present invention. As illustrated in FIGS. 13-15, the distraction tool 60 distracts and creates spaces between adjacent spinous processes. Once distracted, the spinous process fusion implant may be inserted utilizing a spinous process fusion insertion instrument as illustrated in FIGS. 16-20.

Figure 18:
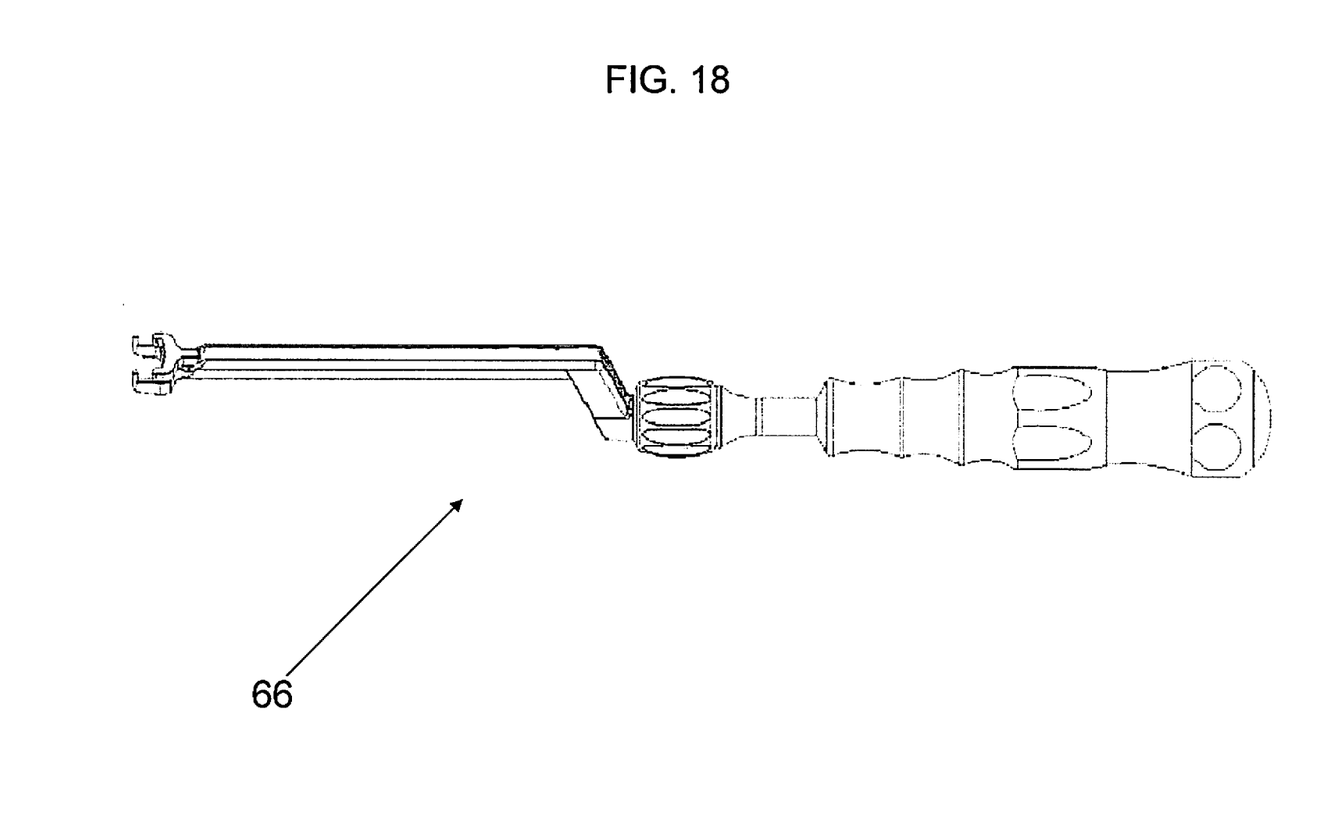
FIG. 18 illustrates an instrument for positioning the second wing or locking plate of the spinous process fusion device according to the present invention.
Figure 19:
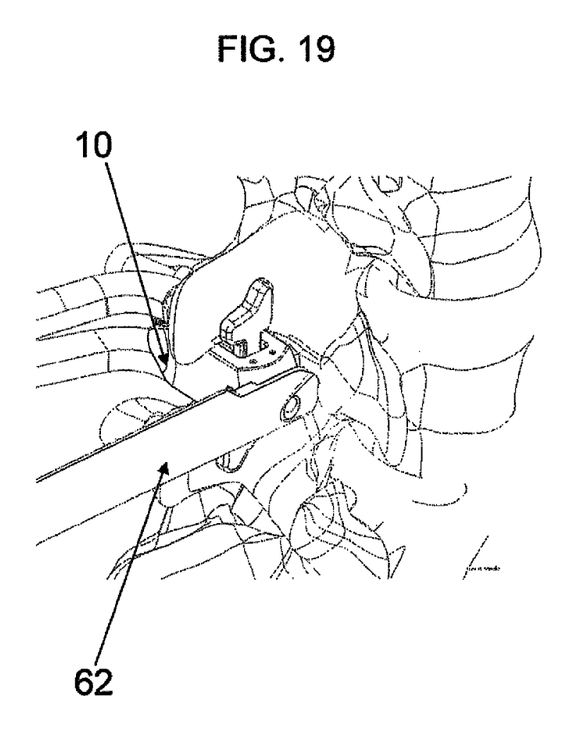
FIGS. 19 and 20 illustrate the positioning and implantation of the spinous process fusion device according to the present invention.
Figure 20:
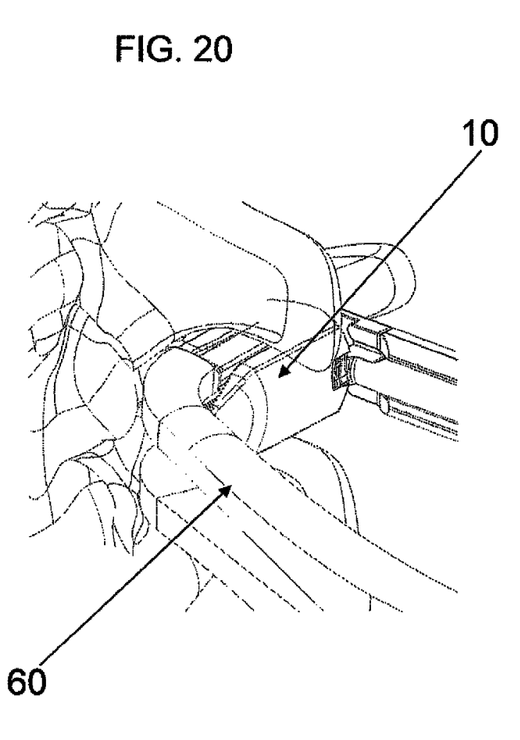

Turning to FIGS. 16-20, additional instruments used in implanting the fusion implant are disclosed. First, implant insertion instrument 62 is adapted to be coupled with the implant 10. Once the ratcheting rod is positioned with a channel provided in the implant insertion instrument 62, a connection knob 64 of the insertion instrument 62 is rotated to firmly couple the ratcheting rod to the insertion instrument 62. The tip of the ratcheting rod is then introduced into the distracted interspinous space and advanced until the spikes of the pivoting plate or first wing are touching the spinous processes. The locking plate or second wing is then introduced into the interspinous space using a plate insertion instrument 66, as illustrated in FIG. 18. The locking plate is lined up with the tip of the ratcheting rod and squeezed until the locking plate is captured by the ratcheting rod members. Next, a compressor instrument may be positioned over both the ratcheting rod and the locking plate and squeezed, advancing the compressor instrument until the spikes of the locking plate are firmly seated in the spinous processes. For additional bite or to accommodate varying spinous process thickness, a plate pincher instrument may be used to sink the plate teeth deeper into the spinous processes, as illustrated in FIGS. 19 and 20.

The spinous process fusion device 10 may comprise, for example, any of a variety of biocompatible materials, including metals, ceramic materials, and polymers. Examples of biocompatible materials include titanium, stainless steel, aluminum, cobalt-chromium, alloys, and polyethylene. By way of example, one or more components (e.g., central barrel, central core, etc.) of the device 10 may comprise polyetheretherketone.

While it is apparent that the invention disclosed herein is well calculated to fulfill the objects stated above, it will be appreciated that numerous modifications and embodiments may be devised by those skilled in the art.

What is claimed is:

1. An implantable device comprising:
    a rod, the rod having a first portion and second portion;
    a first wing coupled to the rod on the first portion;
    a second wing having an opening and being engageable to the rod through the opening;
    a central barrel having a first side and a second side, which extend on either side of the rod, the first side comprising at least one insertion instrument connecting portion and the second side having at least one insertion instrument connecting portion;
    an insertion instrument configured to couple to the first side and the second side of the central barrel; and
    a compressor instrument configured to couple to the rod and the second wing,
    wherein a cam ratcheting lock secures the second wing to the rod via rotation of the rod
    wherein the central barrel is configured to be positioned in an interspinous space.

2. The implantable device of claim 1, wherein the rod is configured to have ratchet receivers on opposing sides adapted to couple with ratcheting members associated with the second wing.

3. The implantable device of claim 2, wherein the ratchet receivers are arranged along a longitudinal axis of the rod.

4. The implantable device of claim 2, wherein the ratchet receivers of the rod when in a first position engage the one or more ratcheting members and when in a second position the ratchet receivers disengage from the one or more ratcheting members.

5. The implantable device of claim 4, wherein the rod is actuated 90 degrees to move from the first position to the second position.

6. The implantable device of claim 4, wherein the first portion of the rod comprises a head configured to receive an insertion instrument and an actuation instrument.

7. The implantable device of claim 1, wherein the first wing has a cutout for stacking more than one of the implantable devices.

8. The implantable device of claim 1, wherein the first wing angulates about a longitudinal axis of the first wing.

9. The implantable device of claim 1, wherein the first wing is rotatably connected to the rod.

10. The implantable device of claim 1, wherein the central barrel is configured to distract adjacent spinous processes.

11. An implantable device:
    a rod comprising opposing protuberances arranged along a longitudinal axis of the rod;
    a wing comprising an opening and ratcheting members on an interior wall of the opening, wherein the rod is disposed through the opening such that the ratcheting members engage the protuberances to secure the wing on the rod at a first position and disengage with the protuberances at a second position via rotation of the rod
    a central barrel having a first side and a second side, which extend on either side of the rod, the first side comprising at least one insertion instrument connecting portion and the second side having at least one insertion instrument connecting portion;
    an insertion instrument configured to couple to the first side and the second side of the central barrel; and
    a compressor instrument configured to couple to the rod and the second wing,
    wherein the central barrel is configured to be positioned in an interspinous space.

12. The implantable device of claim 11, wherein the rod is actuated 90 degrees to move from the first position to the second position.

13. The implantable device of claim 11, wherein the implantable device further comprises a second wing coupled to the rod, and wherein the second wing comprises teeth on a surface of the second wing facing the wing.

14. The implantable device of claim 11, wherein the rod is tapered to a frustoconical tip.

* * * * *